United States Patent
Simonov et al.

(10) Patent No.: US 9,280,000 B2
(45) Date of Patent: Mar. 8, 2016

(54) ADJUSTABLE CHIRAL OPHTHALMIC LENS

(75) Inventors: Aleksey Nikolaevich Simonov, The Hague (NL); Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 82 days.

(21) Appl. No.: 13/579,415

(22) PCT Filed: Feb. 17, 2011

(86) PCT No.: PCT/NL2011/050113
§ 371 (c)(1),
(2), (4) Date: Oct. 23, 2012

(87) PCT Pub. No.: WO2011/102719
PCT Pub. Date: Aug. 25, 2011

(65) Prior Publication Data
US 2013/0138208 A1    May 30, 2013

(30) Foreign Application Priority Data

Feb. 17, 2010   (NL) .................................. 2004255

(51) Int. Cl.
*A61F 2/16*    (2006.01)
*G02C 7/02*    (2006.01)
(Continued)

(52) U.S. Cl.
CPC . *G02C 7/022* (2013.01); *A61F 2/16* (2013.01); *A61F 2/1624* (2013.01); *G02B 3/08* (2013.01);
(Continued)

(58) Field of Classification Search
CPC . A61F 2/16; A61F 2/1613; A61F 2003/0093; A61F 2250/0053; G02B 3/00; G02B 3/0081; G02B 3/02

USPC ................................................ 623/6.11, 6.32
See application file for complete search history.

(56) References Cited

U.S. PATENT DOCUMENTS

| | | |
|---|---|---|
| 3,305,294 A | 2/1967 | Alvarez |
| 3,583,790 A | 6/1971 | Baker |

(Continued)

FOREIGN PATENT DOCUMENTS

| | | |
|---|---|---|
| AU | 2002219861 A8 | 7/2002 |
| DE | 10241208 A1 | 3/2004 |

(Continued)

OTHER PUBLICATIONS

Bernet et al., Adjustable refractive power from diffractive moiré elements, Applied Optics, Jul. 2008, 3722-3730, 47-21.

(Continued)

*Primary Examiner* — David H Willse
*Assistant Examiner* — Javier Blanco
(74) *Attorney, Agent, or Firm* — The Webb Law Firm

(57) ABSTRACT

The present invention relates to an adjustable ophthalmic lens comprising at least one optical element comprising a combination of at least two optical surfaces wherein both optical surfaces are chiral optical surfaces adapted to provide chiral modulation of the light beam, the combination of the chiral optical surfaces is adapted to provide at least one adjustable focus and the combination of the chiral optical surfaces is adapted such that the focal distance of the adjustable foci depends on the mutual position of the chiral optical surfaces. These chiral optical surfaces result in a chiral modulation of the light beam. Combinations of chiral optical surfaces are applied to obtain adjustable optical powers in single-focus ophthalmic lenses and multiple-focus ophthalmic lenses.

7 Claims, 4 Drawing Sheets

(51) Int. Cl.
*G02B 3/08* (2006.01)
*G02C 7/04* (2006.01)
*G02C 7/06* (2006.01)
*G02C 7/08* (2006.01)

(52) U.S. Cl.
CPC *G02C 7/02* (2013.01); *G02C 7/028* (2013.01); *G02C 7/04* (2013.01); *G02C 7/041* (2013.01); *G02C 7/06* (2013.01); *G02C 7/061* (2013.01); *G02C 7/068* (2013.01); *G02C 7/08* (2013.01); *A61F 2/1613* (2013.01); *A61F 2250/0053* (2013.01)

(56) References Cited

U.S. PATENT DOCUMENTS

| | | |
|---|---|---|
| 4,650,292 A | 3/1987 | Baker et al. |
| 5,173,723 A | 12/1992 | Volk |
| 5,748,371 A | 5/1998 | Cathey, Jr. et al. |
| 5,800,533 A | 9/1998 | Eggleston et al. |
| 6,344,937 B1 | 2/2002 | Sparrold et al. |
| 7,018,410 B1 | 3/2006 | Vazeen |
| 2003/0169944 A1 | 9/2003 | Dowski, Jr. et al. |
| 2003/0225455 A1 | 12/2003 | Cathey, Jr. |
| 2004/0145808 A1 | 7/2004 | Cathey, Jr. et al. |
| 2005/0264886 A1 | 12/2005 | Dowski, Jr. |
| 2006/0192919 A1 | 8/2006 | Lindacher |
| 2008/0046076 A1 | 2/2008 | Rombach |
| 2008/0151184 A1 | 6/2008 | Spivey et al. |
| 2008/0312738 A1 | 12/2008 | Wanders |
| 2009/0062912 A1 | 3/2009 | Rombach |
| 2009/0088841 A1 | 4/2009 | Hong et al. |
| 2009/0251663 A1* | 10/2009 | Warden et al. ............... 351/177 |
| 2010/0094413 A1 | 4/2010 | Rombach et al. |
| 2010/0134869 A1 | 6/2010 | Bernet et al. |
| 2010/0280609 A1 | 11/2010 | Simonov et al. |
| 2012/0323321 A1 | 12/2012 | Simonov et al. |

FOREIGN PATENT DOCUMENTS

| | | |
|---|---|---|
| EP | 0187177 A1 | 7/1986 |
| EP | 1433415 A2 | 6/2004 |
| EP | 1692558 | 8/2006 |
| EP | 1932492 A1 | 6/2008 |
| EP | 2044905 A2 | 4/2009 |
| JP | 2005521898 A | 7/2005 |
| JP | 2007526077 A | 9/2007 |
| NL | 1029037 C2 | 11/2006 |
| WO | 9206400 A1 | 4/1992 |
| WO | 9957599 A1 | 11/1999 |
| WO | 0108605 A1 | 2/2001 |
| WO | 0203126 A1 | 1/2002 |
| WO | 03021333 A1 | 3/2003 |
| WO | 2005054927 A2 | 6/2005 |
| WO | 2007015640 A1 | 2/2007 |
| WO | 2007037690 A2 | 4/2007 |
| WO | 2007037691 A2 | 4/2007 |
| WO | 2008077795 A2 | 7/2008 |
| WO | 2009012789 A1 | 1/2009 |
| WO | 2009099598 A1 | 8/2009 |

OTHER PUBLICATIONS

Petitjean, Chiral mixtures, Journal of Mathematical Physics, Aug. 2002, 4147-4157, 43-8.

Salomon et al., Continous symmetry measures: A note in proof of the folding/unfolding method, Journal of Mathematical Chemistry, 1999, 295-308, 25.

Dowski, Jr. et al., Extended Depth of Field Through Wave-Front Coding, Applied Optics, 1995, pp. 1859-1866, vol. 32, No. 11.

Noll, Zernike Polynomials and Atmospheric Turbulence, J. Opt. Soc. Am., 1976, pp. 207-211, vol. 66, No. 3.

Porter et al., Adaptive Optics for Vision Science: Principles, Practices, Design, and Applications, Wiley-Interscience.

Rege et al., Application of the Alvarez-Humphrey Concept to the Design of a Miniaturized Scanning Microscope, Optics Express, 2004, pp. 2574-2588, vol. 12, No. 12.

Simonov et al., Cubic Optical Elements for an Accomodative Intraocular Lens, Optics Express, 2006, pp. 7757-7775, vol. 14, No. 17.

Simonov et al., Varifocal Optics for a Novel Accommodative Intraocular Lens, Proc. of SPIE, 2006, pp. 61130B-1-61130B-7, vol. 6113.

Tyson, Principles of Adaptive Optics, CRC Press, 2010, pp. 14, Third Edition.

* cited by examiner

ADJUSTABLE CHIRAL OPHTHALMIC LENS

BACKGROUND OF THE INVENTION

Ophthalmic lenses (also: "OLs") correct for optical errors of the eye, for example refractive errors such as myopia, hyperopia and presbyopia as well as other errors such as astigmatism. OLs can be positioned outside the human eye as, for example, spectacle lenses or contact lenses, which OLs can be monofocal (with one focal distance), multifocal (with multiple focal distances) or progressive (with a range of focal distances). Monofocal OLs provide sharp vision at a single focal distance and are most common, for example, as reading spectacles and most contact lenses. Multifocal OLs provide at least two foci, for example, bi-focal spectacles and multifocal contact lenses, or, alternatively, provide a continuous range of focal distances, as in, for example, progressive spectacles.

Intraocular lenses (also: "IOLs") are OLs which are positioned inside the human eye and which can be monofocal, multifocal, progressive and accommodating (with variable focus). The inventions set forth in the present document can be applied to all OLs, for example spectacles, for example bi-focal spectacles; IOLs will be used henceforth to illustrate the principles and embodiments of said lenses.

IOLs are generally implanted by a surgeon after removal of the natural lens. Monofocal IOLs, diffractive and refractive multifocal IOLs providing multiple (generally two or three foci) are most common. Accommodating IOLs, providing a variable focus and driven by the accommodative process of the eye, are in development.

IOLs can be monofocal, providing monofocality, having a single focal distance. Monofocal IOLs in combination with the natural optical elements of the eye allow to project a single sharp image of a single object plane on the retina. IOLs can also be multifocal, providing multifocality, having multiple distinct focal distances. With multifocal IOLs a mix of multiple sharp images of multiple object planes on the retina can be obtained. Additionally, the focal distance of the lens can be fixed at manufacturing, as in fixed focus monofocal IOLs, or as in fixed multifocal IOLs. Alternatively, the focal distances of the IOLs can be adjustable as in adjustable focus monofocal OLs (of which the single focal distance is adjustable) and adjustable multifocal IOLs (of which at least one focal distance is adjustable). Accommodating IOLs have a fixed focal distance at the resting state (in an emmetrope eye) and a variable focal distance at the accommodative state. In accommodation the focal distance of the IOL depends on the degree of accommodation of the eye. In adjustable accommodating IOLs the fixed focal distance of the lens is adjustable which is important for obtaining emmetropia.

Diffractive IOLs combine a plurality of diffractive zones to provide multifocality. Diffractive multifocal IOLs have a large number of steep transition zones which zones cause significant image degradation due to scattering of light. In some cases diffractive IOLs may project ghost images, i. e. unwanted diffractive orders, on the retina leading to serious disorders in visual perception.

Refractive multifocal IOLs do not result in image degradation caused by scattering because of smooth surfaces and a limited number of transition zones. Such refractive multifocal IOLs include designs with a plurality of optical zones as in US2006192919 and WO2007037690, designs with radial-symmetry as in WO0108605 and WO9206400, designs with aspheric optical surfaces and with sloping optical surfaces along the azimuth as in WO0203126 and DE10241208 and designs including a smooth cubic phase mask as in US2003225455.

Chiral Optical Surfaces

A chiral optical surface is a surface of an optical element providing chiral phase modulation of light. For example, a chiral surface of a refractive optical element made of a material with a constant refractive index is a chiral optical surface. In mathematical terms, a three-dimensional surface is defined to be chiral if it is not invariant under parity transformation. This means that the mirror image of the surface can not be mapped onto the original by any rotations and translations, see FIG. 2. Definitions of chirality are given, for example, by M. Petitjean (J. Math. Phys. 43, 4147-4157, 2002) and Salomon et al. (J. Mater. Chem. 25, 295-308, 1999), both documents are included in this document by reference. The degree of chirality can be quantified in terms of topological charge or continuous chirality measure.

Chiral optical surfaces, in the context of this document, are characterized by certain steepness in radial and azimuthal directions. The steepness can progress either linearly or non-linearly according to any function which does not break the required chiral symmetry of the surface. Chiral optical surfaces can also include, but not necessarily so, at least one transition zone, for example, as shown in FIG. 3.

A chiral optical surface can be constructed from virtually any optical shape including parabolic, spherical, prismatic shapes etc. For example, consider a cubic surface defined by $$z = S_U(x,y) = U(axy^2 + bx^3/3) \quad (1)$$

in the coordinate system OXYZ, see FIG. 1, with the Z axis along the optical axis; U is the surface steepness measured, for example, in $[mm^{-2}]$; a and b are the dimensionless constants, usually a=b when the X- and Y-axes have equal scales. According to U.S. Pat. No. 3,305,294, a pair of such cubic elements (a=b), mutually shifted along the X axis, can produce a variable-focus lens. Applying parity transformations $(x,y) \to (-x,y)$ or $(x,y) \to (x,-y)$, it can be easily found that this surface is not chiral. However, a combination of the two cubic surfaces can be made chiral, for example, a composite surface defined by $$z = \begin{cases} S_{U_1}(x+x_0, y), & y \geq 0 \\ S_{U_2}(x-x_0, y), & y < 0 \end{cases} \quad (2)$$

where $x_0$ is the constant of shift, $U_1$ and $U_2$ are the surface steepness parameters (generally $U_1 \neq U_2$), is a chiral surface. The surface defined by Eq. (2) is shown in FIG. 4.

By analogy with US2003225455, which describes one cubic surface on one optical element for an extended depth of field (EDF) intraocular lens, it can be noted that the chiral composite surface defined by Eq. (2) also provides continuous multifocality, or EDF. The multifocality ranges are determined by the parameters $U_1$ and $U_2$ in combination with $x_0$ and can be chosen different providing two distinct multifocality zones (along the optical axis). Similarly, with an optical element comprising three cubic surfaces three distinct multifocality zones can be obtained etc.

The man skilled in the art can easily conclude that the combination (as in U.S. Pat. No. 3,305,294) of an optical surface defined by Eq. (2) with a cubic optical surface given by Eq. (1), as shown in FIG. 5, results in a lens with two distinct foci. These foci can be separated along the optical axis, Z-axis, and in the XY-plane (when linear tilt, i. e. wedge prism, is added to one of the optical surfaces).

Mathematical Framework

Assuming that a pair of identical optical elements is superimposed to form a variable-focus lens centred at the point O' and, in cylindrical coordinates, each of the elements is specified by the function $$z = S(r, \theta), \quad (3)$$

where z is the thickness of the element, r is the radius and θ is the polar angle and the point O' characterized by the vector $r_0$ is the centre of the optical surface with the area D, see FIG. 1. Let O be the centre of rotation, then if one element is rotated by +Δθ and another element is rotated by −Δθ the resulting thickness becomes $$\Delta z = S(r, \theta + \Delta\theta) - S(r, \theta - \Delta\theta). \quad (4)$$

Taking the rotation-dependent thickness of a resulting variable-focus lens in the form $$\Delta z = \Delta\theta A (r - r_0)^2, \quad (5)$$

i. e. the optical power of the lens changes linearly with Δθ, A being the amplitude coefficient, applying Taylor expansions to Eqs. 4 and 5 it can be found $$\Delta\vartheta A(r - r_0)^2 = S(r, \vartheta + \Delta\vartheta) - S(r, \vartheta - \Delta\vartheta) \quad (6)$$

$$\cong 2\Delta\vartheta \frac{\partial S(r, \vartheta)}{\partial \vartheta} + 2\frac{(\Delta\vartheta)^3}{3!} \frac{\partial^3 S(r, \vartheta)}{\partial \vartheta^3} + \ldots$$

Note that if $|\theta| \ll 1$ Eq. (5) simplifies to $$\Delta z = \Delta\theta A(r - r_0)^2 \equiv \Delta\theta A(r^2 + r_0^2 - 2rr_0[1 - \theta^2/2]). \quad (7)$$

The approximation of the unknown function $S(r,\theta)$ at $|\theta| \ll 1$ can be determined from the differential equation $$\frac{\partial S(r, \vartheta)}{\partial \vartheta} = \frac{A}{2}(r^2 + r_0^2 - 2rr_0[1 - \vartheta^2/2]). \quad (8)$$

The general solution of Eq. (8) takes the form $$S(r, \vartheta) = \frac{A}{2}(r - r_0)^2 \vartheta + \frac{Arr_0}{6}\vartheta^3 + C, \quad (9)$$

where C is the integration constant. Using Eq. (9) the resulting thickness given by Eq. (4) becomes $$\Delta z = \Delta\vartheta A(r^2 + r_0^2 - 2rr_0[1 - \vartheta^2/2]) + \frac{(\Delta\vartheta)^3 A}{3} rr_0. \quad (10)$$

The residual term $(\Delta\theta)^3 \, Arr_0/3$ is a cone with a vertex at the origin O. The steepness of the cone changes cubically along with Δθ.

Consider now an extreme case when the centre of rotation O is located at infinity, or $|r|, |r_0| \to \infty$. In this case the rotation is equivalent to a linear shift which is convenient to represent in Cartesian coordinates $$x = r \sin\theta \to r\theta$$

$$y = (r - r_0)\cos\theta \to (r - r_0)' \quad (11)$$

Eq. (9) to take the form $$z = S(r, \vartheta) \to \tilde{S}(x, y) \quad (12)$$

$$= \frac{A}{2r_0}(x^3/3 + xy^2) + C.$$

which coincides with the main term of cubic surfaces described in U.S. Pat. No. 3,305,294 by L. Alvarez. A pair of Alvarez elements, being reciprocally displaced, produces a variable-focus parabolic lens with the optical power changing linearly with the lateral shift.

In another extreme, when the centre of rotation O coincides with the lens centre O', or $r_0=0$, Eq. (9) simplifies to $$S(r, \vartheta) = \frac{A}{2}r^2\vartheta + C, \quad (13)$$

and the resulting angle-depended thickness, as defined by Eq. (4), becomes $$\Delta z = \Delta\theta A r^2. \quad (14)$$

Equation (13) determines the thickness of a parabolic screw-type chiral optical element. In the simplest configuration when one surface of the optical element is flat, another surface is a parabolic screw-type chiral surface, or alternatively, a parabolic chiral optical surface, as illustrated in FIG. 3.

It should be noted that implementations of adjustable refractive power from rotation have been described in a prior art document "Adjustable refractive power from diffractive moiré elements," by S. Bernet and M. Ritsch-Marte, Appl. Optics 47, 3722-3730 (2008), which document is included in the present document by reference. However, the authors limited the study to diffractive optical elements (DOEs) only. Their design resulted in a varifocal Fresnel lens with an additional sector lens of a different optical power. An optimized DOE design was suggested to avoid the additional sector lens.

As seen from Eq. (14), the optical power of a variable-focus lens centered at O' is proportional to ΔθA and changes linearly with the angle of rotation Δθ. However, this expression is valid only for the angular sector $\Delta\theta \leq \theta < 2\pi - \Delta\theta$. The sectors $0 \leq \theta < \Delta\theta$ and $2\pi - \Delta\theta \leq \theta < 2\pi$ result in an optical power proportional to ΔθA−πA. So, the variable-focus lens with two mutually rotated screw-type chiral optical elements produces two distinct foci, see FIGS. 7-9. Note also that the light intensities in the foci are proportional to 2(π−Δθ) and 2Δθ respectively.

For example, using formulas from W. J. Smith, *Modern Optical Engineering*, 3-rd. ed. (McGraw-Hill, New York, 2000), the optical power Φ, i. e. inverse focal length, of the lens combination comprising two mutually rotated screw-type chiral optical elements made of a material with the index of refraction n becomes $$\Phi_1 = 2(n-1)\Delta\theta A, \quad (15)$$

when $\Delta\theta \leq \theta < 2\pi - \Delta\theta$ and $$\Phi_2 = 2(n-1)(\Delta\theta - \pi)A, \quad (16)$$

when $0 \leq \theta < \Delta\theta$ and $2\pi - \Delta\theta \leq \theta < 2\pi$.

It can be proven mathematically that a single chiral optical element with the thickness function according to Eq. (13) produces an effective multifocality, i. e. EDF. Making use of the general expression for the optical transfer function (OTF) of an incoherent optical system, i. e. an eye with an implanted chiral optical element, see J. W. Goodman, *Introduction to Fourier Optics*, (Roberts & Company, 2005), in the paraxial approximation it can be easily found that $$H(\omega_r,\omega_\alpha,\phi) \cong H(\omega_r,\omega_\alpha+2\phi/A,0), \quad (17)$$

where H is the defocused OTF, $\phi$ is the defocus parameter (see J. W. Goodman for explanations), and $\omega_r$ and $\omega_\alpha$ are the spatial frequency in polar coordinates $$\omega_x = \omega_y \cos \omega_\alpha,$$

$$\omega_x = \omega_y \sin \omega_\alpha, \quad (18)$$

where $\omega_x$ and $\omega_y$ are the corresponding spatial frequencies in the Cartesian coordinates. So, as seen from Eq. (17), defocusing does not lead to degradation of the resulting image (on the retina) but only rotation of the image. This rotation can be made very small by maximizing the steepness parameter A. FIG. 6 represents an ophthalmic lens comprising a single chiral optical element with continuous multifocality.

SUMMARY OF THE INVENTION

The present invention discloses adjustable monofocal and multifocal ophthalmic lenses which comprise chiral optical surfaces providing a chiral modulation of the light beam. Chiral optics are particularly suited for this application and not even hinted at in any prior art document.

[1] The lens disclosed in the present document comprises a combination of at least two, chiral optical surfaces both adapted to provide chiral modulation of the light beam. The combination is adapted to provide, at least one, adjustable focus (one focus, as in an adjustable monofocal lens and, alternatively, multiple foci, as in an adjustable multifocal lens), and the combination is adapted such that the degree of adjustment of the focus depends on the mutual position of the chiral optical surfaces. Definitions of chiral surfaces and mathematical treatments thereof are provided in separate sections elsewhere in the present document. Such lenses can have nearly continuous free-form optical surfaces with a limited number of transition zones, or, diffractive optical surfaces with multiple transition zones, or, combinations of said optical surfaces. Free-form surfaces, in the context of the present document, are optical surfaces which may have at most only one axis of symmetry, X or Y, which axis excludes the optical axis (Z).

[2, 3] The lens can comprise at least two optical elements each comprising a chiral optical surface and the mutual positions of at least two optical elements can he adjusted. This embodiment is intended for postoperative adjustment of the lens by a surgeon. Alternatively, the lens can comprise one optical element comprising at least two chiral optical surfaces of which the mutual position is fixed after manufacturing of the optical clement. This alternative embodiment allows a lens manufacturer to adjust the lens optical power using the same set of chiral surfaces. For example, two chiral surfaces of a single-element ophthalmic lens can be manufactured with a different relative position.

The lens can be such that the focal distance can be adjusted only once and remain fixed thereafter. Such lenses can comprise, for example, at least one, optical element with a combination of, at least two, chiral optical surfaces which combination provides, at least one, fixed focus. The distance of the focus depends on the design, steepness of chiral optical surfaces, and on relative position of the chiral surfaces which can remain fixed after manufacturing of the lens. The chiral surfaces can be combined on one surface of the element, or, the chiral surfaces can be distributed over two surfaces of the same optical element. In this case the thickness function of the chiral element can be defined by Eq. (13) derived in the section "Mathematical framework", see also explanation after Eq. (16) and the corresponding FIG. 6.

[4] The lens generally also comprises at least one correction optical surface adapted to provide correction of, at least one, aberration of the eye, for example refractive error or any other aberration, for example astigmatism, or, alternatively, correcting any aberration caused by the lens itself. Such aberrations can remain after application of a lens correcting only for refractive error, or that residual aberration remain, for example due to measuring errors, or that such residual errors develop over time because of refractive drift of the eye with aging. Such correction surfaces are common for all current ophthalmic lenses.

[5, 6] The lens can be adjusted by adjustment of the mutual rotational position of the chiral optical elements around any axis parallel to the optical axis in the XY-plane, the plane which extends perpendicular to the optical axis, the Z-axis. Such lens can remain adjustable also after manufacturing. Note that rotation can be any rotation leading to the general formula Eq. (10) for the thickness function of an optical element, with, for example, the rotation axis along the optical axis resulting in the thickness function according to Eq. (13), or, on the rim of the optical elements (also: fan-like rotation with the thickness function given by Eq. (10)), or, at infinity (also: shift of the optical elements) resulting in the thickness function according to Eq. (12). A preferred rotational position is the position in which the chiral optical elements are located concentrically and that the rotation is rotation around the central axis of the chiral optical elements.

Adjustable multifocality refers to adjustable focal distances but also to adjustable focal intensities which intensities depend on the focal distances. The total light intensity remains the same, but the distribution of intensities over foci can differ. The relative intensity of the focal spots also depends on the mutual rotational angle between the optical elements. In the present document the emphasis is placed on the adjustable focal distances because of practical applications. However, the combinations of chiral optical surfaces can be designed such that certain focal distances are combined with certain focal intensities, for example, a short focal distance can be combined with a high focal intensity to support reading at low light levels, or, alternatively, a long focal distance can be combined with high focal intensity to support driving at night.

The two chiral optical surfaces can be combined with correcting optical surfaces and are positioned on separate physical sides of the one element intraocular lens, but said surfaces can also be combined on only one physical side, for example in an annular design. Note that additional, traditional, focusing optics covering only part of the light beam can be added to provide for additional foci, for example a small central reading lens, for example, covering the point of origin.

[7, 8] An adjustable opththalmic lens can be an adjustable ophthalmic monofocal lens comprising at least one optical element comprising at least one correction optical surface and at least two chiral optical surfaces, or, alternatively, an adjustable opththalmic lens can be an adjustable ophthalmic monofocal lens comprising at least two optical elements comprising at least one correction optical surface and at least two chiral optical surfaces.

An adjustable opththalmic lens can be an adjustable ophthalmic multifocal lens comprising at least one optical element comprising at least one correction optical surface and at least two chiral optical surfaces, or, alternatively, an adjustable opththalmic lens can be an adjustable ophthalmic multifocal lens comprising at least two optical elements comprising at least one correction optical surface and at least two chiral optical surfaces. Chiral optical surfaces included in an ophthalmic lens can include at least one transition zone, and chiral optical surfaces for multifocal optical arrangements adapted to provide multifocality must include at least one transition zone which must be combined with additional transition zones of additional chiral optical surfaces. So, a combination of at least two chiral optical surfaces including at least one transition zone included in each chiral optical surface, with transition zones in a non-overlapping configuration, is required to provide multifocality.

For example, for adjustable multifocal lenses, a combination of two chiral optical surfaces can be adapted such that the combination provides adjustability and projects, at one extreme position of the optical elements, two foci of equal intensity and, at the other extreme position of the elements, one single focus with an intensity equal to the combined said two foci, i. e. the total energy remains constant irrespective of distribution over the optical axis. Radial extended transition zones in parallel on the same axis which do not overlap provide for two foci of equal intensity by combining a discrete sector, for example, discrete halve, of each chiral optical surface with a discrete sector of another chiral optical surface. Radial extended transition zones in parallel on the same axis with complete overlap provide one focus and the optical function of the multifocal arrangement is reduced to a planar function because the chiral modulation of chiral elements of opposite signs cancel each other out. In the case of parabolic chiral optical surfaces the parabolic function, in this example a focusing function, might remain and add to the total focusing power of the ophthalmic lens in combination with the focusing power of additional correction optical arrangement. Rotational positions of the transition zones in between these extremes will result in variable relative intensities of the foci, with one focus decreasing in intensity in accordance with clockwise rotation, the other focus in accordance with counter-clockwise rotation. Such adjustable multifocal lens provides ample freedom for adjustment. For example, an adjustable discrete multifocality can provide a discrete multifocal lens with, for example, two foci, for example, one focusing the eye at a distance and one at a reading distance, of which the relative intensity can be adjusted, providing a lens for distance vision only, or a lens for reading vision only, or a lens for any combination of distance vision and reading vision in between these extremes.

The distance of the foci depends on the design, steepness, of the chiral optical surfaces but, most important, on the relative position of the chiral surfaces, which can be a relative rotational position. So, adjustment can be achieved by rotating the optical elements versus each other. Said rotation can be any rotation, including rotation with the rotation axis positioned on the optical elements, for example, positioned in the centre of the optical elements, in a configuration resembling a cart-wheel, or on the rim of the optical elements, in a configuration resembling a fan, an example of such fan-like construction illustrated in, for example, EP0187177, or rotation with the rotation axis positioned outside of the optical elements, a configuration providing a dominantly fan-like rotation at close distances and, at increasing distance, a configuration providing a combination of fan-like rotation and shift, eventually providing, at infinite distance, a pure linear shift of the optical elements, with chiral optical surfaces adapted to provide for desired optical functions for said specific rotational configurations.

An optical element comprises two optical sides with shapes according to at least one optical function, for example, a free-form surface, for example, a chiral surface or at least one cubic surface which surface can be combined with a, for example, a parabolic surface or a spherical lens surface, or with a planar surface.

The lens can be an adjustable intraocular ophthalmic lens, adjustable intraocular lens, adjustable IOL, which lens can be an adjustable monofocal intraocular lens or, alternatively, an adjustable multifocal intraocular lens, of which lenses the relative position of the optical elements is adjusted occasionally, by external means, for example, a yearly adjustment by an eye-surgeon to adjust the lens for, for example, refractive drift of the eye. IOLs are implanted in the eye by a surgeon to correct optical disorders of the eye, for example, to correct for presbyopia. Monofocal intraocular lenses project one sharp, in-focus, sharp, image on the retina. Multifocal intraocular lenses project multiple overlapping sharp images of multiple object planes simultaneously, for example, two overlapping sharp images of an object at a close distance and an object at a larger distance. Patients with monofocal lenses generally require progressive spectacles for sharp vision over an extended range, patients with multifocal lenses generally require monofocal spectacles, patients with accommodative IOLs are generally spectacle free. So, IOLs can thus be constructed according to the descriptions disclosed in the present document for implantation in the human eye to provide a combination of at least two foci, multifocality, and correction of at least one optical disorder of the eye. Alternatively, the lens can be fitted in a construction which construction is adapted to provide continuous adjustment of the optical elements by the accommodative process of the eye itself allowing the eye to accommodate.

[9] At least one chiral optical surface of the ophthalmic lens (disclosed in the present document) may comprise a parabolic chiral surface, or parabolic screw-type chiral surface, as shown in FIG. 3. Such parabolic chiral surface, taking alone, provides optical multifocality, i. e. EDF. Two parabolic surfaces can provide adjustable multifocality, or, in case of optical diffractive elements, adjustable single focus and can be included in ophthalmic lenses of a thin design. The chiral optical surfaces can be asymmetrical, largely free-form optical surfaces, preferably parabolic chiral optical surfaces which have proven to provide quality optics because of an absence of zero values in the spatial spectrum, usually in the neighborhood of the zero region of the spectrum, which preserves information, alternatively, provides a maximum S/N ratio (meaning, for example, low light scattering). The two chiral optical surfaces are of opposite chirality, alternatively, right-handed or left-handed, but not necessarily of equal steepness. The preferred embodiment includes chiral optical surfaces with a shape according to $z=Ar^2\theta$ within the circular pupil of the eye, with z the surface sag, r the radial coordinate, $\theta$ the polar angle in the plane of the surface, and A the mask steepness, or, in alternative coordinates, according to $z=\Phi(r, \theta)=Ar^2\theta$, defined in a pupil of a unit radius, with r the radial coordinate and, in this notation, $\theta$ the polar angle in the transverse plane. Degrees of steepness, polar angle, and rotation of the chiral optical surfaces relative provide design parameters with angular steepness, which is in this context the partial derivative with respect to the polar angle being linear or non-linear which also applies to radial steepness, which is in this context the partial derivative with respect to the radius. The chiral optical surface includes a central point of origin and a radial transition zone which is not chiral. So, alternatively, a chiral optical surface can be composed which does not include said point of origin nor the transition zone. An adapted cubic surface can be chiral optical surfaces, as shown in FIG. 4, to be included in lenses disclosed in the present document, or, alternatively, any other chiral surfaces can be chiral optical surfaces to be included in lenses disclosed in the present document.

[10, 11] Said adjustable ophthalmic lenses can include at least one chiral optical surface which surface can be a diffractive chiral optical surface, or alternatively, which surface can be a refractive chiral optical surface, or, alternatively, a combination of optical surfaces can include at least one diffractive optical surface and at least one refractive optical surface. Reflective, mirror-like, surfaces can be adapted to provide chiral modulation, and such surfaces remain an option to be included in ophthalmic lenses, however, reflective surfaces are, at present, not practical to be included in ophthalmic lenses.

[12, 13] Adjustable intraocular ophthalmic lens construction can comprise chiral intraocular optics including at least one chiral optical surface as described in the present document and also positioning means (also: haptics) to position the lens construction in the human eye.

Also, an adjustable spectacle construction can comprise spectacle optics and positioning means (also: spectacle frame) to position the spectacle construction in front of the human eye with the spectacle construction comprising at least one chiral spectacle lens including at least one chiral optical surface as described in the present document.

A single chiral surface providing chiral modulation, or, alternatively, multiple chiral surfaces of which the transition zones precisely overlap, can be adapted to provide continuous multifocality, a range of gradually increasing focal distances projecting the image on the retina simultaneously. Such lenses support projection of an infinite number equally sharp images of a defined continuous range of object planes on the retina. Continuous multifocality is referred to as Extended Depth of Focus (EDF) in the technical literature. EDF results in, a generally minor, overall blur of the image and consequently in reduced image contrast. A single chiral optical surface with one transition zone, or a completely smooth chiral optical surface, with no transition zones, provides continuous multifocality, as do multiple chiral optical surfaces of which the transition zones precisely overlap. So, combinations of ophthalmic lenses which have no transition zones, or limited number of transition zones, can provide continuous multifocality with an effect comparable to the lens disclosed in US2003225455 which lens comprises not chiral optical surfaces but a single cubic optical surface. So, continuous multifocality can be provided by an ophthalmic lens including at least one optical element. The range over which the sharpness stretches along the optical axis and the degree of sharpness along said range depends mainly on the steepness parameter of the chiral optical surface. The focal distance of the range, i. e. a distance defined as, for example, the distance of centre of the range to the principal plane of the ophthalmic lens, depends mainly on the focusing power of correcting optics in combination with the focusing power of the eye. Such continuous multifocal lenses can be adapted as ophthalmic lenses, OLs, including intraocular lenses, IOLs.

Note also that combinations of chiral optical surfaces with different degrees of steepness, of opposite sign, will provide combinations of discrete multifocality and continuous multifocality, which combinations, albeit complex combinations, can be adapted to fit complex requirements of particular eyes.

More than two chiral surfaces distributed over at least two optical elements can be adapted to provide an adjustable continuous multifocal lens in which the dimensions of the range of sharpness can be varied in a fixed combination with the degree of sharpness, for example from a limited range in the direction of the optical axis in combination with a relative high degree of sharpness to an extended range along the optical axis in combination with a relative low degree of sharpness, or, in alternative terms, extension of range in the direction of the optical axis, the Z-direction will result in extension of range in the direction of the X- or Y-axis or in a direction of a combination thereof.

Ophthalmic lenses set forth above can be positioned in front of the eye, for example as a spectacle lens, with the lens fitted with required positioning means, for example, a spectacle frame, or positioned on top of the eye, as a contact lens, with the lens fitted with required positioning means, for example, a contact lens rim to fit the cornea, or positioned and fixed in a suitable position inside the eye, as an intraocular lens, in the anterior chamber of the eye or in the posterior chamber of the eye, as a phakic IOL or as an aphakic IOL fitted with required positioning means, for example, haptics. Alternatively, the chiral surfaces can be distributed over different vision aids as in: spectacles can comprise one chiral surface and a contact lens the other chiral surface, or, alternatively, spectacles one chiral surface and an intraocular lens the other chiral surface, or, alternatively, the intraocular lens one chiral surface and a contact lens the other chiral surface.

Multifocal ophthalmic lenses disclosed in the present document can comprise refractive optical arrangements as in traditional spectacle lenses, contact lenses and intraocular lenses, or comprise reflective optical arrangements, as in, for example, intraocular telescopes for treatment of macular dystrophy, as in, for example, U.S. Pat. No. 7,008,448 and WO03082155 or diffractive optical arrangements as in diffractive multifocal intraocular lenses, or combinations of refractive, reflective and diffractive optical arrangements.

DETAILED DESCRIPTION OF THE PREFERRED EMBODIMENTS

Figure 1:
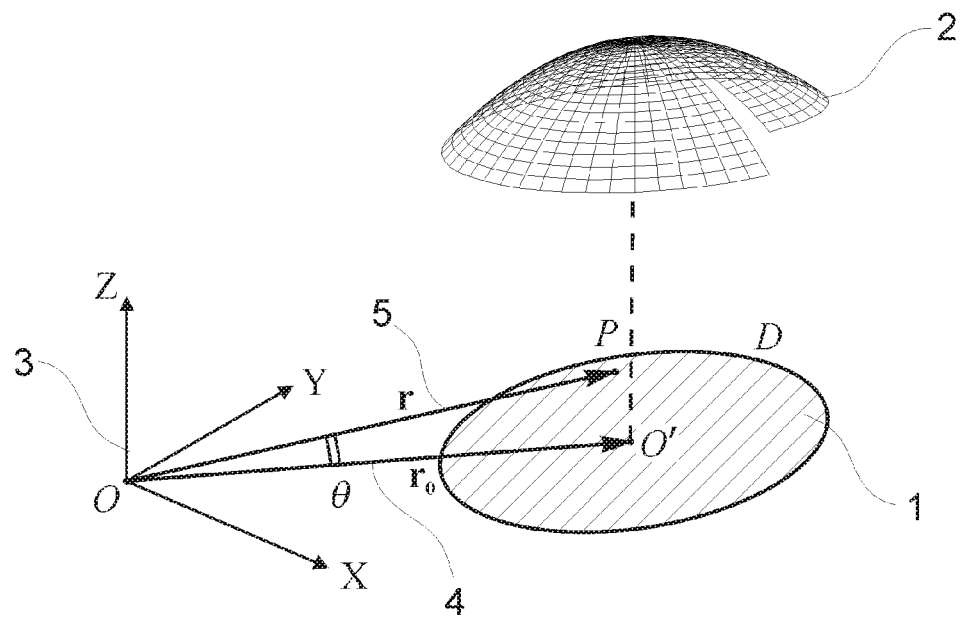
FIG. 1 shows the projection of a cubic optical surface into a coordinate plane.

FIG. 1 shows a projection, 1, of an optical surface, 2, onto the XY plane of the coordinate system OXYZ, 3. The radius-vector $r_0$, 4, connects the point of origin O of the coordinate system with the centre O' of the projected area D. The radius-vector r, 5, denotes the coordinate of an arbitrary point P within D. The angle θ is the angle between r and $r_0$.

Figure 2:
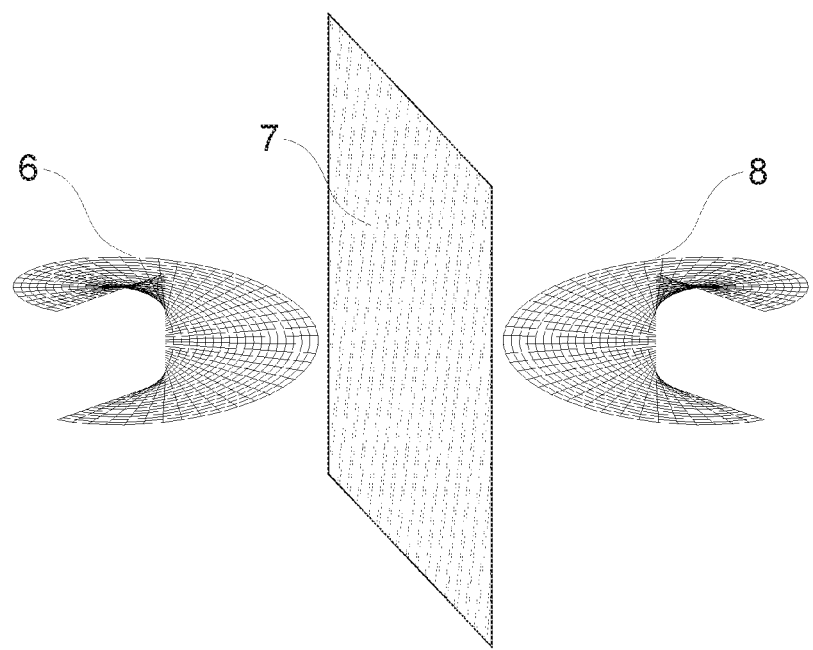
FIG. 2 shows a linear screw-type chiral surface and its mirror image to display its chirality.

FIG. 2 shows a chiral surface, 6, in this example a linear screw-type chiral surface with counter-clockwise chirality in front of a flat mirror, 7. The mirrored image of the chiral surface, 8, is a linear screw-type surface in a clockwise direction. Owing to chirality, the mirrored image can not be superimposed on the original by any combination of rotation and translation.

Figure 3:
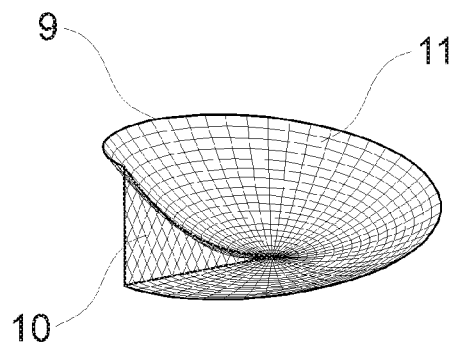
FIG. 3 shows a parabolic screw-type chiral surface with a transition zone.

FIG. 3 shows a parabolic screw-type chiral surface, 9, in this example with counter-clockwise chirality, with a transition zone, 10, and smooth chiral surface, 11.

Figure 4:
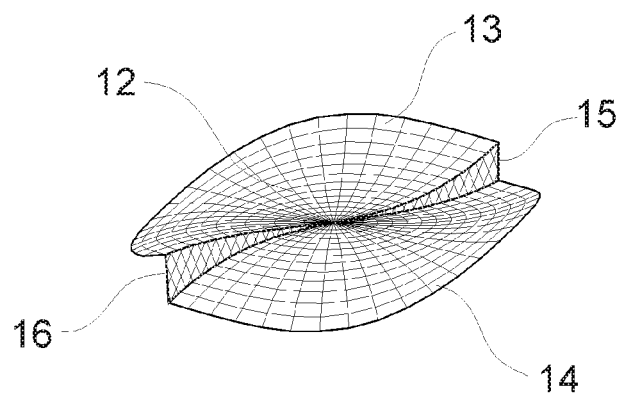
FIG. 4 shows a chiral surface composed of two smooth, laterally shifted cubic surfaces.

FIG. 4 shows a chiral surface, 12, composed, in this example, of two smooth, laterally shifted cubic surfaces, 13 and 14, with transition zones, 15 and 16.

Figure 5:
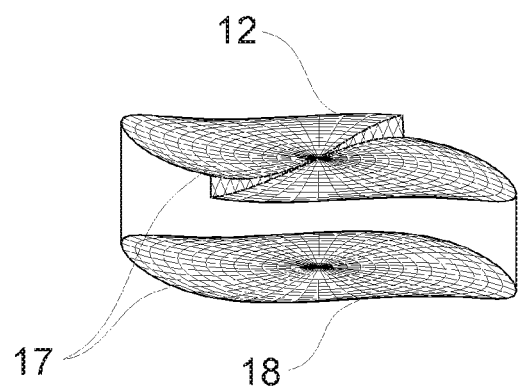
FIG. 5 shows an ophthalmic lens producing two discrete foci and comprising of a chiral surface, explained in FIG. 4 and a smooth cubic surface.

FIG. 5 shows two optical surfaces of an ophthalmic lens producing two discrete foci and comprising two optical surfaces 17, consisting of the chiral surface, 12, explained in FIG. 4 and a smooth cubic surface, 18.

Figure 6:
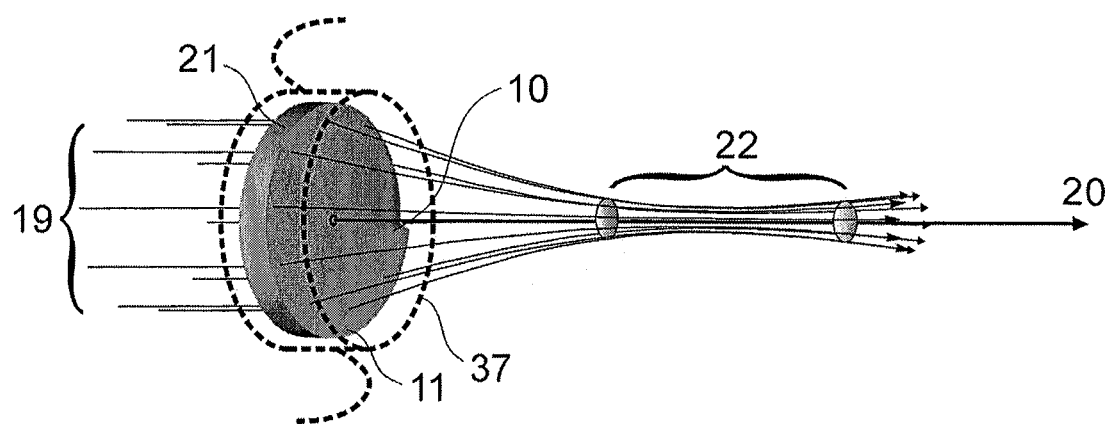
FIG. 6 shows a parabolic screw-type chiral ophthalmic lens providing continuous multifocality.

FIG. 6 shows an optical element, 21, of an ophthalmic lens, 37, providing continuous multifocality, illuminated by a collimated light beam (depicted as a bundle of rays), 19, propagating along the optical axis, 20, and passing through the optical element, 21, in this example with a parabolic screw-type chiral surface, with transition zone, 10, and smooth chiral surface, 11. The optical element produces an extended, continuous range of defocus, 22. The construction of the ophthalmic lens, 37, illustrates schematically positioning means (also: haptics) to position the lens construction in the human eye.

Figure 7:
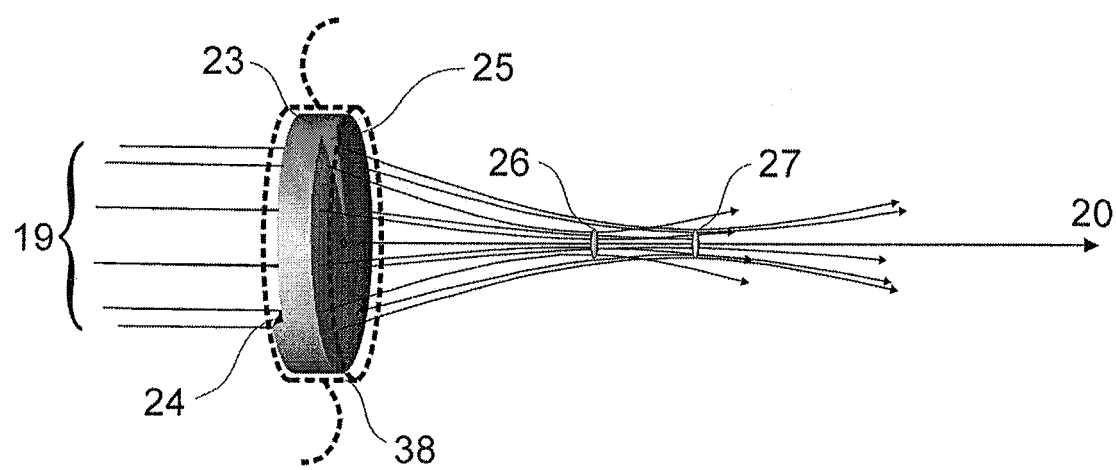
FIG. 7 shows a chiral ophthalmic lens comprising two parabolic screw-type surfaces providing discrete multifocality.

FIG. 7 shows an optical element, 23, of an ophthalmic lens, 38, providing discrete multifocality, illuminated by a collimated light beam (depicted as a bundle of rays), 19, propagating along the optical axis, 20, and passing through the optical element, 23, in this example the optical element comprising two parabolic screw-type surfaces, with angularly non-overlapping transition zones, 24 and 25, on the anterior and posterior surfaces, respectively. After refraction by the optical element the light rays converge towards two discrete foci, 26 and 27, along the optical axis. The construction of the ophthalmic lens, 38, illustrates schematically positioning means (also: haptics) to position the lens construction in the human eye.

Figure 8:
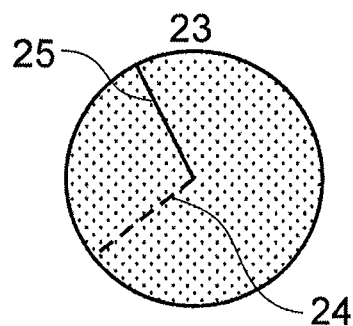
FIG. 8 shows the front view of the ophthalmic lens depicted in FIG. 7.

FIG. 8 shows the front view of the optical element, 23, of the ophthalmic lens, 38, depicted in FIG. 7 with two non-overlapping transition zones on the anterior and posterior surfaces. The dashed line, 24, represents the transition zone on the anterior surface of the lens and a solid line, 25, represents the transition zone on the posterior surface of the optical element. The construction of the ophthalmic lens, 38, illustrates schematically positioning means (also: haptics) to position the lens construction in the human eye.

Figure 9:
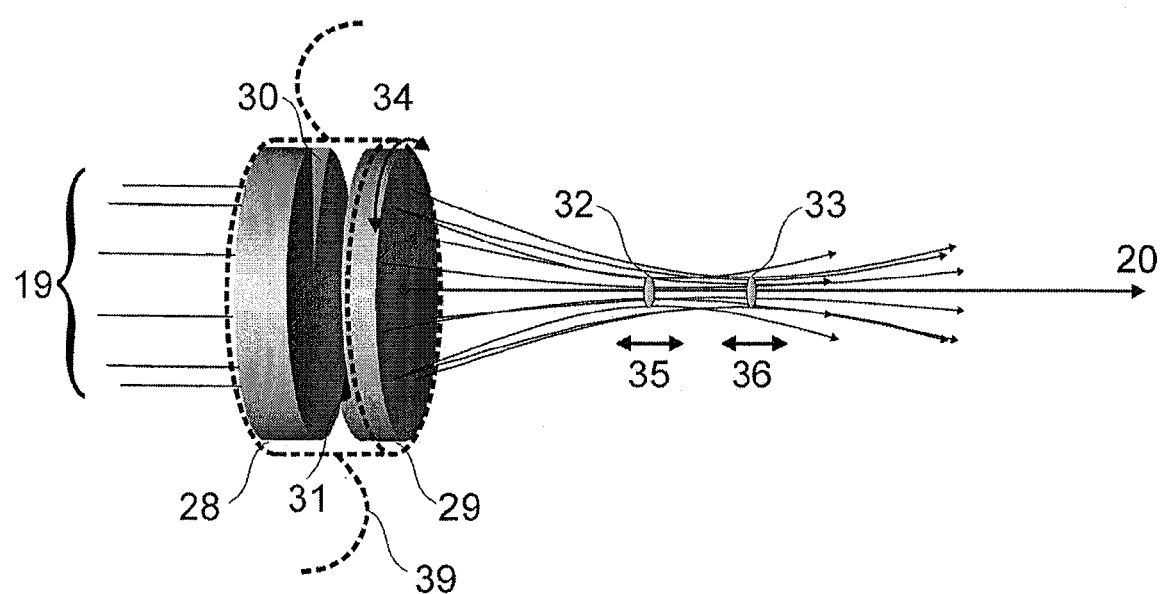
FIG. 9 shows an ophthalmic lens providing for adjustable multifocality with an anterior chiral element and a rotatable posterior chiral element.

FIG. 9 shows two optical elements of an ophthalmic lens, 39, providing adjustable multifocality, illuminated by a collimated light beam (depicted as a bundle of rays), 19, propagating along the optical axis, 20, and passing through an anterior chiral optical element, 28, and a posterior chiral optical element, 29, with angularly non-overlapping transition zones, 30 and 31. The optical elements produces two discrete foci, 32 and 33, in the direction of the optical axis. In this example each optical element of the lens comprises a parabolic screw surface and the posterior element is used for adjustability—by its rotation, 34, the refractive power of the multifocal lens can be adjusted in a way that the focal regions move simultaneously, 35 and 36, along the optical axis. The construction of the ophthalmic lens, 39, illustrates schematically positioning means (also: haptics) to position the lens construction in the human eye.

The invention claimed is:

1. An intraocular lens (IOL) comprising:
    at least one optical element comprising a first chiral optical surface and a second chiral optical surface;
    wherein the at least one optical element is adapted to provide chiral modulation of a light beam passing through the at least one optical element;
    wherein the optical surfaces are adapted to provide at least one adjustable focus;
    wherein the combination of the chiral optical surfaces is adapted such that a focal distance of the adjustable focus depends on a mutual position of the chiral optical surfaces;
    wherein each optical surface is a nearly continuous free-form refractive surface with a number of transition zones not exceeding one; and
    wherein at least one of the chiral optical surfaces comprises a parabolic screw-type chiral surface.

2. The lens of claim 1, comprising two optical elements;
    wherein a combination of the optical elements is adapted to provide adjustable focus; and
    wherein a focal distance of the adjustable focus depends on a mutual position of the optical elements.

3. The lens of claim 2, wherein at least one optical element comprises at least one cubic optical surface.

4. The lens of claim 2, wherein at least one optical element comprises at least one correcting optical surface to correct at least one aberration of an eye.

5. The lens of claim 2, wherein the mutual position of the optical elements is a rotational position of the optical elements relative to optical axes of the optical elements or an axis parallel to the optical axis of an eye.

6. The lens according to claim 2, wherein the lens is an adjustable multifocal lens.

7. The lens according to claim 1, wherein the lens comprises positioning means to position the IOL in a human eye by a surgeon.

* * * * *